US00PP21189P2

(12) United States Plant Patent
Smith

(10) Patent No.: US PP21,189 P2
(45) Date of Patent: Aug. 10, 2010

(54) ***ASTER* PLANT NAMED 'PINK YOHENRY THE THIRD'**

(50) Latin Name: *Aster hybrida*
Varietal Denomination: Pink Yohenry the Third

(75) Inventor: Mark A. Smith, Fort Myers, FL (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/460,107

(22) Filed: Jul. 14, 2009

(51) Int. Cl.
*A01H 5/00* (2006.01)

(52) U.S. Cl. ..... Plt./355

(58) Field of Classification Search ..... Plt./355
See application file for complete search history.

*Primary Examiner*—Kent L Bell
(74) *Attorney, Agent, or Firm*—S. Matthew Edwards

(57) ABSTRACT

A new *Aster* plant named 'Pink Yohenry the Third', particularly distinguished by the upright, medium size, freely branching growth habit, dark green foliage, and purple-light purple flowers.

1 Drawing Sheet

Latin name of the genus and species of the plant claimed: *Aster hybrida.*

Varietal denomination 'Pink Yohenry the Third'.

BACKGROUND OF THE INVENTION

The present invention comprises a new *Aster*, botanically known as *Aster hybrida,* and hereinafter referred to by the variety name 'Pink Yohenry the Third'.

The new cultivar 'Pink Yohenry the Third' has upright, medium size, freely branching growth habit, dark green foliage, and purple-light purple flowers.

'Pink Yohenry the Third' originates as a natural lateral branch mutation of the cultivar 'Yohenry the Third,' U.S. Plant Pat. No. 19,016. 'Pink Yohenry the Third', was discovered and selected by the inventor as a lateral branch mutation upon one plant within a population of the parent cultivar in a controlled breeding program in Alva, Fla. in March 2006. The parent cultivar 'Yohenry the Third' has purple flower color, is a few days faster to flower under natural season response, and is slightly larger in plant size.

The first act of asexual reproduction of 'Pink Yohenry the Third' was accomplished when vegetative cuttings were propagated from the mutated branch from the original plant in May 2006 in a controlled environment in Alva, Fla.

BRIEF SUMMARY OF INVENTION

Horticultural examination of plants grown from cuttings of the plant initiated in May 2006, and continuing thereafter, has demonstrated that the combination of characteristics as herein disclosed for 'Pink Yohenry the Third' are firmly fixed and are retained through successive generations of asexual reproduction.

'Pink Yohenry the Third' has not been observed under all possible environmental conditions. The phenotype may vary significantly with variations in environment such as temperature, light intensity and day length.

The following traits have been repeatedly observed and are determined to be basic characteristics of the new variety. The combination of these characteristics distinguishes this *Aster* as a new and distinct variety.

A Plant Breeder's Right for this cultivar has not been applied for. 'Pink Yohenry the Third' has not been made publicly available more than one year prior to the filing of this application.

BRIEF DESCRIPTION OF THE PHOTOGRAPHS

The accompanying photographic drawing shows typical flower and foliage characteristics of 'Pink Yohenry the Third' with colors being as true as possible with an illustration of this type. The photographic drawing shows a flowering potted plant of the new variety, and a close-up of the flower.

DETAILED BOTANICAL DESCRIPTION

The plant descriptions, measurements and photographs were taken in Salinas, Calif. in early June 2009 under natural light. These plants were started and grown in Alva, Fla. and were shipped to California in the beginning of June 2009. Plants were grown under conditions which approximate those generally used in commercial potted *Aster* production. These plants used in the photograph and descriptions were about 10-11 weeks old.

Color references are made to The Royal Horticultural Society Colour Chart (R.H.S.) 2001.

TABLE 1

DIFFERENCES BETWEEN THE NEW VARIETY 'PINK YOHENRY THE THIRD' AND A SIMILAR VARIETY

| | 'Pink Yohenry the Third' | 'Pink Milka' (U.S. Plant Pat. No. 12,461) |
|---|---|---|
| Flower color: | Purple-Light purple | Light purple |
| Greenhouse black cloth flowering response: | 1 week slower | 1 week faster |
| Plant habit: | Shorter, fuller and rounder | Taller, less full, less round |

Plant:

*Form, growth and habit.*—Upright, in a somewhat inverted triangle; freely branching.

*Plant height.*—10-12 cm.

*Plant height* (*inflorescence included*).—12-14 cm.
*Plant width.*—22-26 cm.
*Garden performance and tolerance to weather.*—Very good.
*Crop time to flowering.*—About 10 weeks.

Roots:
*Number of days to initiate roots.*—10 days at about 22 degrees C.
*Number of days to produce a rooted cutting.*—16-18 at 22 degrees C.
*Type.*—Fine, fibrous, free branching.
*Color.*—RHS N155B but whiter.

Foliage:
*Arrangement.*—Alternate, simple, sessile.
*Immature, leaf color, upper surface.*—RHS 146A.
*Lower surface.*—RHS 146A.
*Mature, leaf color, upper surface.*—RHS 147A.
*Lower surface.*—RHS 146A.
*Length.*—3.3-3.9 cm.
*Width.*—0.6-0.85 cm.
*Shape.*—Ligulate to ensiform.
*Base shape.*—Clasping.
*Apex shape.*—Acute.
*Margin.*—Slightly serrulate with ciliate.
*Texture, upper surface.*—Slightly hirsute at margin.
*Lower surface.*—Slightly hirsute at margin.
*Color of veins, upper surface.*—Indistinct, or the same color as the leaf.
*Color of veins, lower surface.*—Indistinct, or the same color as the leaf.

Stem:
*Quantity of main branches per plant.*—5-7.
*Quantity of leaves per branch.*—About 10.
*Color of stem.*—Little darker than RHS 147A.
*Length of stem.*—12-16 cm.
*Diameter.*—0.2-0.3 cm.
*Length of internodes.*—0.5-0.8 cm.
*Texture.*—Slightly hirsute.
*Color of peduncle.*—RHS 146A but darker.
*Length of peduncle.*—2.0-2.1 cm.
*Peduncle diameter.*—0.15 cm.
*Orientation to branch.*—About 45 degrees.
*Texture.*—Slightly hirsute.

Inflorescence:
*Type.*—Compositate type, inflorescences borne terminally above and beyond the foliage, ray florets arranged acropetally on a capitulum.
*Blooming habit.*—Under natural flowering conditions, plants flower in mid to late September in the Northern Hemisphere.
*Average quantity of inflorescences per plant.*—About 90.
*Lastingness of individual blooms on the plant.*—About 5 weeks.
*Fragrance.*—None.

Bud (just before opening/showing color):
*Color.*—RHS 77D.
*Length.*—0.7-0.8 cm.
*Width.*—0.6-0.8 cm.
*Shape.*—Ovoid.

Immature inflorescence:
*Diameter.*—2.0-2.3 cm.
*Color of ray florets.*—RHS N78B, with RHS N78A basally and RHS 77A at the apex.

Mature inflorescence:
*Diameter.*—2.9-3.1 cm.
*Depth.*—1.3-1.5 cm.
*Total disc diameter.*—0.3 cm or less.
*Receptacle height.*—0.5-0.6 cm.
*Receptacle diameter.*—0.4-0.5 cm.

Ray florets:
*Average quantity of florets.*—About 90 in numerous whorls.
*Color of florets, upper surface.*—RHS N78B; maturing to about RHS 76D overlaid with a little RHS 77C.
*Lower surface.*—RHS 76C.
*Length.*—1.3-1.4 cm.
*Width.*—0.2-0.25 cm.
*Shape.*—Elliptical to narrowly oblanceolate.
*Apex shape.*—Obtuse to slightly praemorse.
*Margin.*—Entire.
*Texture, upper surface.*—Papillose.
*Lower surface.*—Papillose.

Disc florets:
*Average quantity of disc florets.*—None observed.

Phyllareis:
*Quantity.*—About 40 in numerous whorls.
*Color, upper surface.*—Between RHS 147A and RHS 147B.
*Lower surface.*—Between RHS 147A and RHS 147B.
*Length.*—0.5 cm.
*Width.*—0.1 cm.
*Shape.*—Lanceolate.
*Apex shape.*—Acute.
*Based.*—Fused.
*Margins.*—Entire.
*Texture, upper surface.*—Mostly glabrous and glossy, with some hirsute mainly on the margins.
*Lower surface.*—Mostly glabrous and glossy, with some hirsute mainly on the margins.

Reproductive organs:
*Gynoecium.*—Present on ray florets only (as no disc florets were observed).
*Pistil quantity.*—1.
*Length.*—0.5-0.6 cm.
*Style color.*—RHS 155B.
*Style length.*—0.4-0.5 cm.
*Stigma color.*—RHS 4D, some RHS 155B.
*Stigma shape.*—Bi-parted.
*Androecium.*—Not observed.
*Fertility/seed set.*—Has not been observed on this hybrid.

Disease/pest resistance: Disease resistance or susceptibility has not been observed on this hybrid.

What is claimed is:

1. A new and distinct variety of *Aster* plant named 'Pink Yohenry the Third', substantially as illustrated and described herein.

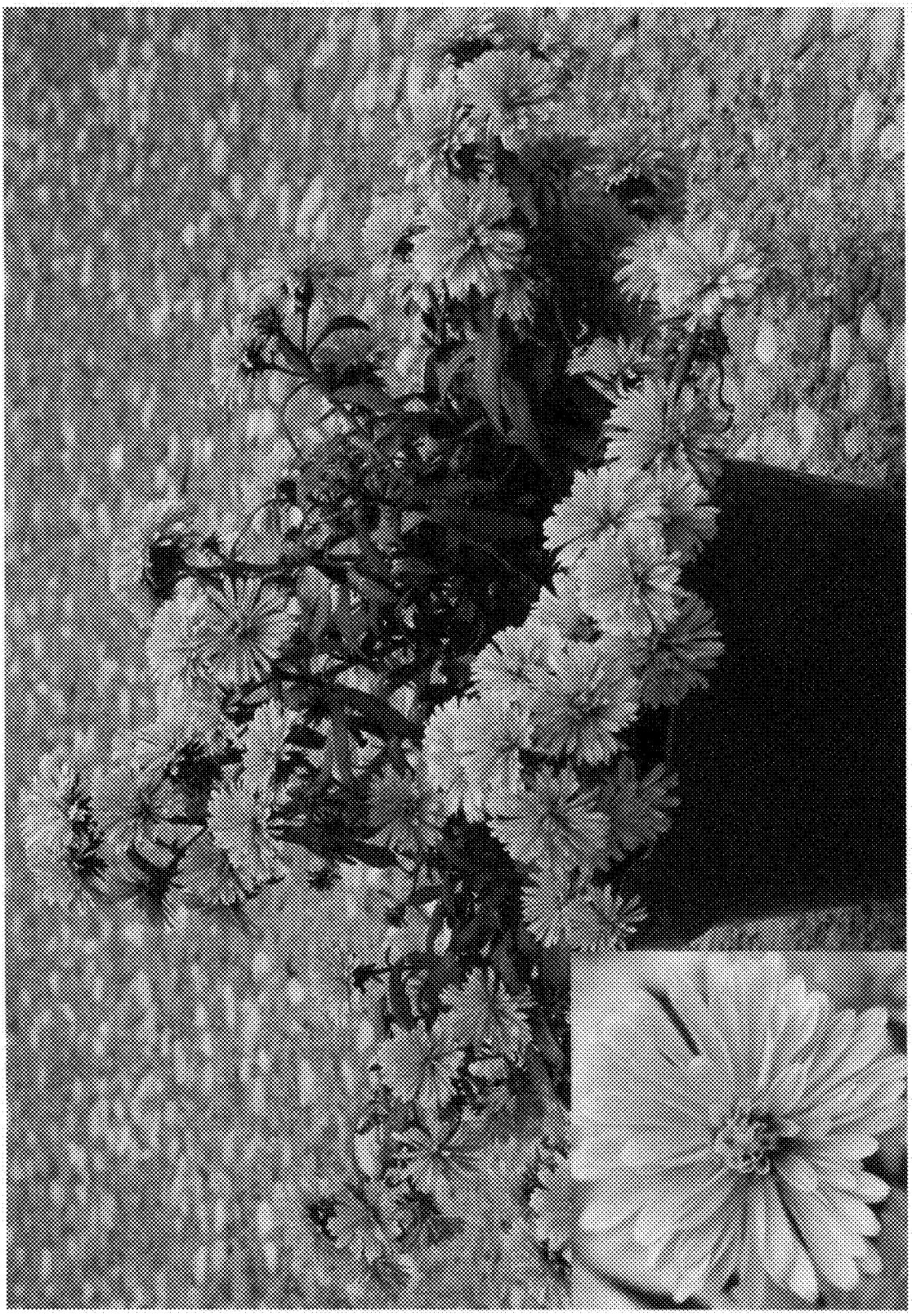

* * * * *